US00PP16370P2

(12) United States Plant Patent
Strope

(10) Patent No.: US PP16,370 P2
(45) Date of Patent: Mar. 21, 2006

(54) **NEW GUINEA *IMPATIENS* PLANT NAMED 'BALCELIPURT'**

(50) Latin Name: *Impatiens hawkeri*
Varietal Denomination: Balcelipurt

(76) Inventor: Kerry Strope, 508 Hough St., Jefferson City, MO (US) 65101

( * ) Notice: Subject to any disclaimer, the term of this patent is extended or adjusted under 35 U.S.C. 154(b) by 175 days.

(21) Appl. No.: 10/741,698

(22) Filed: Dec. 19, 2003

(51) Int. Cl.
*A01H 5/00* (2006.01)

(52) U.S. Cl. ..... Plt./318

(58) Field of Classification Search ..... Plt./318
See application file for complete search history.

*Primary Examiner*—Kent Bell
(74) *Attorney, Agent, or Firm*—Wood, Phillips, Katz, Clark & Mortimer

(57) ABSTRACT

A new and distinct cultivar of New Guinea *Impatiens* plant named 'Balcelipurt' characterized by its large light purple-colored flowers with darker purple-colored mid-rib, medium green-colored foliage, uniform medium upright, mounded growth habit, and good basal branching.

1 Drawing Sheet

Latin name of genus and species of plant claimed: *Impatiens hawkeri.*
Variety denomination: 'Balcelipurt'.

BACKGROUND OF THE INVENTION

The present invention relates to a new and distinct New Guinea *Impatiens* plant botanically known as *Impatiens hawkeri* and hereinafter referred to by the cultivar name 'Balcelipurt'.

The new cultivar was developed by the inventor in a controlled breeding program during June 2000 at Arroyo Grande, Calif. The objective of the breeding program was to develop New Guinea *Impatiens* cultivars with numerous large flowers, excellent basal branching, and upright compact to moderate growth habits.

The female (seed) parent of 'Balcelipurt' was the commercially available *Impatiens hawkeri* cultivar 'Toga' (U.S. Plant Pat. No. 10,304) characterized by its compact upright growth habit, light lavender-colored flowers, and dark green-colored foliage. The male (pollen) parent of 'Balcelipurt' was 'BFP-796' (U.S. Plant Pat. No. 11,486), characterized by its vigorous upright habit, apricot-colored flowers and medium green-colored foliage. 'Balcelipurt' was discovered and selected as a single flowering plant within the progeny of the above stated cross-pollination in January of 2001 at Arroyo Grande, Calif. The new *Impatiens* was initially designated '3246-1'.

Asexual reproduction of the new cultivar by terminal stem cuttings taken in West Chicago, Ill., since 2001, has demonstrated that the new cultivar reproduces true to type with all the characteristics, as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

It was repeatedly found that the cultivar of the present invention:

1. Exhibits large round light purple-colored flowers with darker purple-colored mid-rib.
2. Forms medium green-colored foliage,
3. Exhibits a good basal branching character, and
4. Exhibits a medium, upright mounded growth habit.

Plants of the new cultivar differ from plants of the female parent primarily in foliage color and from plants of the male parent primarily in flower color.

Of the many commercially available New Guinea *Impatiens* cultivars known to the inventor, 'Balcelipurt' is most similar to 'Purple Star' (U.S. Plant Pat. No. 10,091). However, in side-by-side comparisons conducted in West Chicago, Ill., plants of the new cultivar differed from plants of 'Purple Star' in the following characteristics:

1. Plants of the new cultivar have larger leaves than plants of 'Purple Star',
2. Plants of the new cultivar have larger flowers than plants of 'Purple Star', and
3. Plants of the new cultivar have less pubescence on the leaves and stems than the plants of 'Purple Star'.

BRIEF DESCRIPTION OF THE PHOTOGRAPH

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcelipurt'. The plants were grown from rooted cuttings for 11 weeks in a greenhouse at West Chicago, Ill.

DETAILED DESCRIPTION

Figure 1:
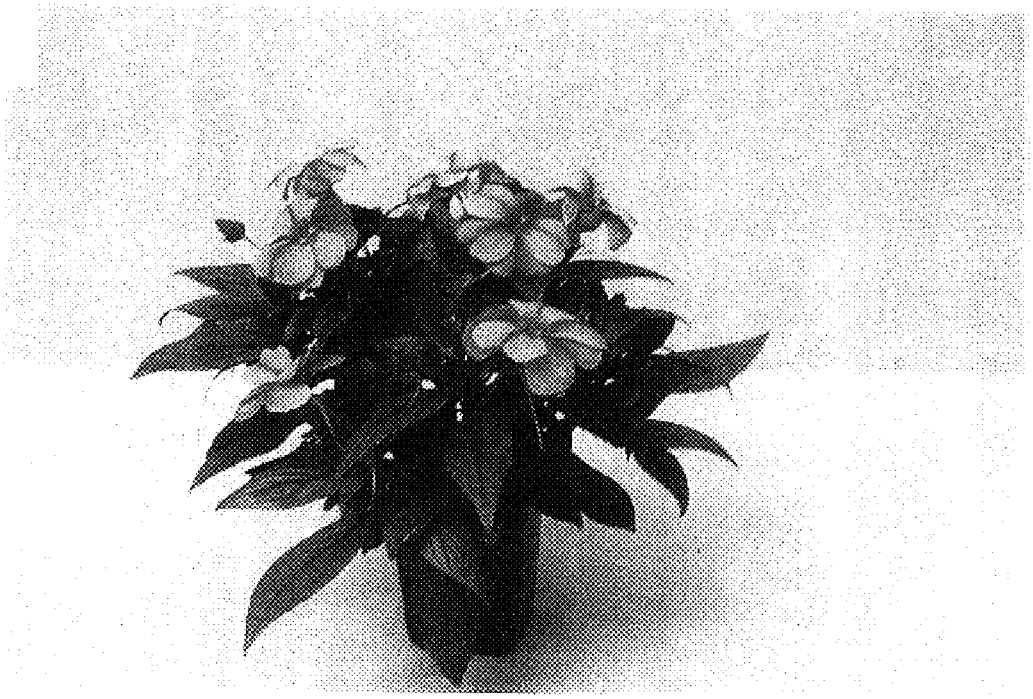
FIG. 1 illustrates a side view of the overall growth and flowering habit of 'Balcelipurt'.
Figure 2:
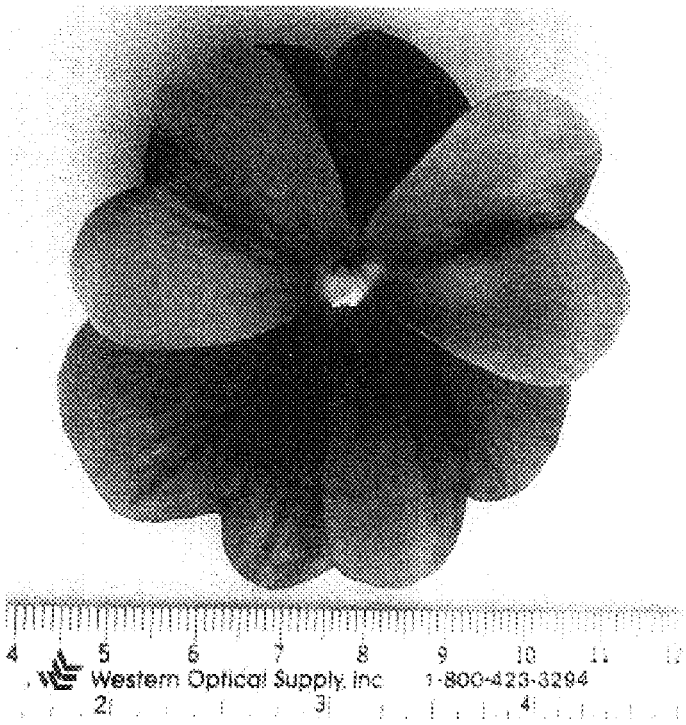
FIG. 2 illustrates a close-up view of a single flower of 'Balcelipurt'.

The chart used in the identification of colors described herein is The R.H.S. Colour Chart of The Royal Horticultural Society, London, England, 1995 edition, except where general color terms of ordinary significance are used. The color values were determined on Sep. 11, 2003 between 1:00 and 1:45 p.m. under natural light conditions.

The following measurements and comparisons describe plants produced from cuttings taken from stock plants and grown in West Chicago, Ill. under greenhouse conditions comparable to those used in commercial practice. The plants were grown in 10 cm pots for 11 weeks utilizing a soilless growth medium. Greenhouse temperatures were maintained at approximately 72° F. during the day and approximately 65° F. during the night. Greenhouse light levels were maintained at approximately 4,000–7,000 footcandles during the day.

Classification: *Impatiens hawkeri* cultivar 'Balcelipurt'.

Parentage:

*Female (seed) parent.*—*Impatiens hawkeri* cultivar 'Toga' (U.S. Plant Pat. No. 10,304).

*Male (pollen) parent.*—*Impatiens hawkeri* cultivar 'BFP-796' (U.S. Plant Pat. No. 11,486).

Propagation:

*Type cutting.*—Terminal stem.

*Time to initiate roots.*—Approximately 7–14 days.

*Time to develop a rooted cutting.*—Approximately 21 days.

*Root description.*—Fine, fibrous.

*Rooting habit.*—Freely branching.

Plant description:

*Habit of growth.*—Moderately vigorous with good basal branching. A mature plant, 11 weeks after the planting of a rooted cutting, commonly measures approximately 22.3 cm from soil level to top of plant plane and approximately 33.3 cm in width (plant spread).

*Plant form.*—Upright and mounded.

*Branches.*—Quantity per plant: Approximately 5. Length: Approximately 13 cm. Diameter: Approximately 9 mm. Texture: Glabrous. Color: 183A. Internode length: Approximately 3.9 cm.

*Foliage.*—Type: Simple. Arrangement of lower leaves: Alternate. Arrangement of upper leaves: Whorls. Shape: Elliptic. Apex: Acuminate. Base: Attenuate. Margin: Serrulate, ciliate. Texture of upper and lower surfaces: Leathery. Pubescence of upper surface: Moderately papillate. Pubescence on lower surface: None. Venation pattern: Pinnate. Size of mature foliage: Length: Approximately 8.7 cm. Width: Approximately 3.6 cm. Color of mature foliage: Upper surface is 139A with veins and mid-vein of 183B. Lower surface is 139B with heavy overlay of 185B and veins and mid-veins of 185A. Petiole: Length: Approximately 2.4 cm. Diameter: Approximately 3 mm. Texture of both upper and lower surface: Glabrous. Color of both upper and lower surface: 185A.

Flower description:

*Flower type.*—Single, not fragrant with self-cleaning petals.

*Flowering habit.*—Freely flowering with flowers positioned above the foliage and facing outward or upward.

*Natural flowering season.*—Year round in greenhouse environment. Flowering is continuous from spring until fall in the garden.

*Lastingness of individual bloom.*—Approximately 10 days.

*Quantity of flowers and buds per stem.*—Approximately 2 fully open flowers and 6 buds at any one time.

*Mature flower buds (just before opening).*—Shape: Ovate. Length: Approximately 1.6 cm. Diameter: Approximately 1 cm. Color of petals: N74D.

*Flower shape.*—Round, flat.

*Flower size.*—Diameter: Approximately 6 cm. Depth: Approximately 1.2 cm.

*Petals.*—Number: Five per flower. Shape: Obovate. Margin: Entire. Apex: Emarginate. Base: Superior petal has truncate base, other four petals have attenuate bases. Texture of upper and lower surfaces: Glabrous. Appearance: Iridescent. Size: Superior petal length: 2.6 cm. Superior petal width: 3.8 cm. Lateral petal length: 3 cm. Lateral petal width: 2.9 cm. Lower petal length: 3.4 cm. Lower petal width: 3.3 cm. Color of upper surface of mature petals: Background between N74B and N74C with mid-rib and margin of N74A. Color of lower surface of petals: Background lighter than N74D with mid-rib and base of 55A.

*Calyx.*—Quantity of sepals: Three, with lower sepal modified into a spur. Sepal shape: Ovate. Sepal texture: Glabrous. Lateral sepal length: Approximately 1.1 cm. Lateral sepal width: Approximately 6 mm. Lateral sepal color of both surfaces: 144C with veins of 63A and overlaid with 184B. Lower sepal length: Approximately 1.4 cm. Lower sepal width: Approximately 1.2 cm. Lower sepal color of both surfaces: 63D with venation of 63A and overlaid with 63B.

*Spur.*—Quantity: One per flower. Length: Approximately 5.3 cm. Diameter at flower: 2.5 mm. Diameter at tip: 0.7 mm. Aspect: Curved downward. Color: 145D with tip of N144B and base of 63C.

*Peduncles.*—Strength: Strong. Angle to stem: Acute. Length: Approximately 5.8 cm. Diameter: 1.5 mm. Texture: Glabrous. Color: N144C at base gradually changing to 184B at base of flower.

*Reproductive organs.*—Androecium: Five stamens, anthers are fused together forming one organ that surrounds the pistil. Filaments are free. Generally, the anthers shed pollen prior to the stigma becoming receptive. Filament color: 155C with upper two overlaid with 63C. Anther shape: Oval. Anther length: 3 mm. Anther color: 4D. Pollen amount: Moderate. Pollen color: 10D. Gynoecium: Pistil number: One per flower. Pistil length: 4 mm. Stigma shape: Five pointed star. Stigma length: 0.5 mm. Stigma color: Translucent. Style length: 0.5 mm. Style color: Translucent. Ovary length: 3 mm. Ovary diameter: 2 mm. Ovary texture: Glabrous. Ovary color: 144A overlaid with N186C.

Seed and fruit development: Neither seed nor fruit production has been observed.

Disease and pest resistance: Resistance to pathogens and pests common to *Impatiens* has not been observed.

What is claimed is:

1. A new and distinct cultivar of New Guinea *Impatiens* plant named 'Balcelipurt' substantially, as herein shown and described, which:

1. Exhibits large round light purple-colored flowers with darker purple-colored mid-rib,
2. Forms medium green-colored foliage,
3. Exhibits a good basal branching character.

* * * * *

UNITED STATES PATENT AND TRADEMARK OFFICE

CERTIFICATE OF CORRECTION

PATENT NO. : PP 16,370 P2
APPLICATION NO. : 10/741698
DATED : March 21, 2006
INVENTOR(S) : Kerry Strope It is certified that error appears in the above-identified patent and that said Letters Patent is hereby corrected as shown below:

Column 4:
Amend the claim to read as follows:

1. A new and distinct cultivar of New Guinea *Impatiens* plant named 'Balcelipurt' substantially, as herein shown and described, which:

1. Exhibits large round light purple-colored flowers with darker purple-colored mid-rib, 2. Forms medium green-colored foliage, 3. Exhibits a good basal branching character, and 4. Exhibits a medium upright mounded growth habit.

Signed and Sealed this

First Day of August, 2006

JON W. DUDAS
*Director of the United States Patent and Trademark Office*